(12) United States Patent
Fischell et al.

(10) Patent No.: US 9,056,025 B2
(45) Date of Patent: Jun. 16, 2015

(54) MEANS AND METHOD FOR PREVENTING EMBOLIZATION OF DRUG ELUTING STENTS

(75) Inventors: Robert E. Fischell, Dayton, MD (US); David R. Fischell, Fair Haven, NJ (US)

(73) Assignee: Svelte Medical Systems, Inc., New Providence, NJ (US)

( * ) Notice: Subject to any disclaimer, the term of this patent is extended or adjusted under 35 U.S.C. 154(b) by 472 days.

(21) Appl. No.: 12/969,134

(22) Filed: Dec. 15, 2010

(65) Prior Publication Data

US 2012/0158116 A1    Jun. 21, 2012

(51) Int. Cl.
*A61F 2/06* (2013.01)
*A61F 2/958* (2013.01)
*A61F 2/962* (2013.01)

(52) U.S. Cl.
CPC ........... *A61F 2/958* (2013.01); *Y10T 29/49826* (2015.01); *A61F 2/962* (2013.01); *A61F 2002/9583* (2013.01)

(58) Field of Classification Search
CPC .. A61F 2/958; A61F 2002/9583; A61F 2/962
USPC ............. 623/1.11, 1.12, 1.13, 1.21; 606/194, 606/198
See application file for complete search history.

(56) References Cited

U.S. PATENT DOCUMENTS

| | | | |
|---|---|---|---|
| 5,108,416 A * | 4/1992 | Ryan et al. | 606/194 |
| 5,810,871 A | 9/1998 | Tuckey et al. | |
| 5,980,530 A * | 11/1999 | Willard et al. | 623/1.11 |
| 6,174,316 B1 * | 1/2001 | Tuckey et al. | 606/108 |
| 6,270,504 B1 * | 8/2001 | Lorentzen Cornelius et al. | 606/108 |
| 6,387,118 B1 * | 5/2002 | Hanson | 623/1.11 |
| 6,510,722 B1 | 1/2003 | Ching et al. | |
| 6,585,747 B1 | 7/2003 | Limon et al. | |
| 7,163,555 B2 | 1/2007 | Dinh | |
| 2002/0038140 A1 * | 3/2002 | Yang et al. | 623/1.12 |
| 2002/0038141 A1 * | 3/2002 | Yang et al. | 623/1.12 |
| 2002/0068966 A1 * | 6/2002 | Holman et al. | 623/1.11 |
| 2002/0072789 A1 * | 6/2002 | Hackett et al. | 623/1.12 |
| 2003/0074044 A1 * | 4/2003 | Randby et al. | 623/1.11 |
| 2003/0149465 A1 * | 8/2003 | Heidner et al. | 623/1.11 |
| 2004/0073250 A1 * | 4/2004 | Pederson et al. | 606/192 |
| 2009/0281617 A1 * | 11/2009 | Cottone et al. | 623/1.23 |
| 2010/0063571 A1 * | 3/2010 | Roach et al. | 623/1.11 |

FOREIGN PATENT DOCUMENTS

| | | |
|---|---|---|
| JP | 2004-305753 | 11/2004 |
| JP | 2010-503465 A | 2/2010 |
| WO | WO-2008033621 A1 | 3/2008 |

OTHER PUBLICATIONS

Written Opinion of the Internation Preliminary Report for Application No. PCT/US2011/064372 dated Nov. 14, 2012.
Japanese Office Action for related Japanese Application No. 2013-544643 dated Jun. 25, 2014.

* cited by examiner

*Primary Examiner* — Katrina Stransky
(74) *Attorney, Agent, or Firm* — Honigman Miller Schwartz and Cohn LLP (57) ABSTRACT

A balloon disposed near a distal end of the catheter tubing and moving between deflated and inflated states, and proximal and distal stent retention bands concentrically arranged around respective proximal and distal end portions of the balloon. The proximal stent retention band has a distal end located within 2 mm of the proximal end of a stent coaxially received by the balloon and the distal stent retention band has a largest diameter within 2 mm of the distal end of the stent received by the balloon.

9 Claims, 3 Drawing Sheets

MEANS AND METHOD FOR PREVENTING EMBOLIZATION OF DRUG ELUTING STENTS

TECHNICAL FIELD

This disclosure relates to stent delivery catheters for placing stents into a blood vessel of a human subject.

BACKGROUND

It is well known to place balloon expandable stents into various vessels of a human subject. At the present time, a variety of stents are being used to act as a scaffold to prop open a stenosis that is situated within an artery. Under certain circumstances, balloon expandable stents have been known to come off their stent delivery catheter during insertion into a patient, which phenomenon is referred to as stent embolization. To prevent stent embolization, the stent is typically crimped and then nested onto the balloon of the stent delivery catheter. The process of crimping is accomplished by applying a radial force in an inward direction to the exterior cylindrical surface of the stent. The crimping force squeezes the stent radially inward against the outer surface of the balloon, compressing the balloon under the struts of the stent. The process of nesting which follows crimping has the crimped stent inserted in and restrained by a heated tube while the balloon under the stent is inflated to an elevated pressure with an inert gas or nitrogen. The inflated balloon is then kept at the elevated temperature for a certain period of time which can be called the "nesting time." For a typical bare metal stent, the crimping force causes the diameter of the balloon under a stent strut to be reduced by approximately 3 mils (1.0 mil is equal to 0.001 inches). The nesting of a bare metal stent is typically accomplished by the application of a temperature of about 95 degrees C., at a pressure into the balloon of about 10 pounds per square inch (psi), for a nesting time period of about 20 seconds. The result of the nesting is to cause the balloon to bulge up into the interstices between the struts of the stent. The bulges then act as a restraining means to prevent longitudinal movement of the stent and thus prevent stent embolization. This phenomenon of the bulging outward of the balloon is clearly seen in FIGS. 2, 3 and 4 of the Fischell et al, U.S. Pat. No. 6,375,660.

The use of crimping and nesting processes is even more important to avoid stein embolization when the stent has certain design features such as wide struts that cannot "dig in" to the balloon material or mostly longitudinal elements that will easily slide along the balloon. An even bigger problem occurs in drug eluting stents where the drug coats the metal stent, e.g., the Cordis Cypher® Stent or the drug elutes from drug reservoirs (holes in the stent) e.g. the Cordis Nevo® Stent. There are several issues here:

1. the drug can be damaged by the elevated pressures used in nesting,
2. the coating itself is relatively soft and delicate thus limiting the pressure that can be used for crimping and
3. even if nesting temperatures that will not damage the drug are used, drug placed in reservoirs will soften from elevated temperatures and may pop out of the holes by the bulging balloon. This can be a significant problem with designs such as the Cordis Nevo® Stent where the wider struts, needed to hold the drug, reduce the ability of the stent to hold onto the balloon as the catheter is advanced into the body.

Fischell, et al in U.S. Pat. Nos. 6,375,660, 6,936,065 and 7,011,673 ("the Fischell patents") each show elastic bands that are placed over the ends of a stent delivery inflatable balloon that would help prevent stent embolization. The bands of the Fischell patents are shown only for use on fixed wire stent delivery systems and are placed up against the distal and proximal ends of the stent which is impractical unless the bands are placed after the stent is crimped onto the balloon. In addition, the Fischell patents teach only that the bands extend just to the ends of the balloon. This construction can create a bump in diameter of the delivery system thereby reducing the deliverability of the system.

SUMMARY

Although this disclosure describes a stem delivery catheter for delivering stents into an artery, the stent delivery catheter may also used to deliver a stent into a variety of vessels of a human body.

There is a significant need for preventing stent embolization for stents where only a small crimping force or lower nesting temperature and pressure are used for mounting a delicate stent onto the balloon of a stent delivery catheter. A "delicate" stent is defined herein as one that could be damaged by either the crimping or the nesting process. This is particularly applicable to drug eluting stents where reduced crimping force and/or reduced nesting parameters would result in a decreased deformation of the balloon onto which the stent is crimped as compared to the forceful crimping and high temperature and pressure nesting, which processes are typically used to retain bare metal stents onto their delivery balloons.

One aspect of the disclosure provides a stent delivery catheter that has a balloon expandable stent including stent retention bands that extend beyond the ends of the balloon combined with a bare or drug eluting stent which is mounted onto the balloon between the stent retention bands using significantly reduced parameters for crimping and/or nesting of the delicate stent. It is typical for such an inflatable balloon to have five separate sections that are described as follows: 1) a central cylindrical section onto which the stent is mounted; 2) a distal cylindrical shaft that fixedly joins the balloon to the distal end of the stent delivery catheter which is typically an inner tube, which is designed to be advanced over a guide wire; 3) a distal conical section connected at its distal end to the to the balloon's distal cylindrical shaft and connected at its proximal end to the central cylindrical section of the balloon; 4) a proximal cylindrical shaft that fixedly joins the balloon to the distal end of an outer tube, which tube forms a lumen with a torroidal cross-section between that outer tube and the inner tube though which fluid can be introduced or removed to inflate and/or deflate the balloon; and 5) a proximal conical section connected at its proximal end to the to the proximal cylindrical shaft of the balloon and connected at its distal end to the central cylindrical section of the balloon.

The present invention is also applicable to fixed wire stent delivery systems where the inner tube would be replaced by a core wire as shown by Fischell, et al, in FIG. 4 of U.S. Pat. No. 7,011,673, which is hereby incorporated by reference in its entirety.

In some implementations, a distal stent retention band prevents the stent from sliding off the stent delivery, catheter in a distal direction and a proximal stent retention band prevents the stent from being moved away from the central cylindrical section of the balloon which can cause part of the stent to not be fully expanded. With the stent mounted onto the central cylindrical section of the balloon, it cannot slide far in either the distal or proximal directions because the retention bands will prevent such a longitudinal displacement of the stent. With this configuration, there will not be embolization of the stein into the patient's arterial system or a significant displacement of the stent off of the central cylindrical section of the balloon, which significant displacement would result in incomplete deployment of the stent into an arterial stenosis. In point of fact, with stent retention bands as taught herein, the stent is restricted in its longitudinal displacement to remain within the confines of the distal and proximal stent retention bands. Because of the presence of the stent retention bands, it is possible to significantly decrease the force required to crimp the stent onto the balloon white still providing good stent retention that prevents stent embolization. Furthermore, it is possible to reduce the temperature and/or pressure and/or nesting time as used for nesting the stent onto the balloon, even to the point of totally eliminating the need for nesting. Thus, comparatively delicate stent coverings can be used that would otherwise be damaged by the typical stent crimping force and/or nesting parameters that are currently used to place most stents onto a balloon. Still further, this means and method can be used to apply an appropriately weak is crimping force and reduced nesting parameters onto a stent that has holes containing a polymer that includes an anti-restenosis drug such as sirolimus so that the polymer containing the drug is not pushed out of such a hole as a result of the crimping and/or nesting. Thus, in some implementations, the stent delivery catheter may include the combination of stent retention bands with a stent that has holes through its struts, which holes contain a polymer with an anti-restenosis drug.

With a typical stent, the crimping force used to place the stent securely onto the balloon so that embolization will not occur will result in a decrease of approximately 3 mils (0.003 inches) of the diameter of the balloon where the struts of the stent are crimped onto that balloon. In some implementations, a light crimping force can be used so that at no place under a stent strut is the balloon diameter after crimping reduced by more than 2.0 mils and preferably less than 1.0 mil. Thus, in some implementations, the stent delivery catheter may include a combination of stent retention bands that prevent stent embolization combined with a stent crimped with decreased crimping force and/or nesting parameters to secure the stent onto the balloon, which weak crimping force and/or nesting parameters would otherwise frequently result in stent embolization. Stilt further, depending on the size of the hole into which a polymer is placed and depending on the polymers sensitivity to temperature, it can be experimentally determined as to what nesting parameters could be used without causing any polymer to be popped out of any hole in the stent struts.

In some implementations, the proximal stent retention band is attached to the outer tube of the stent delivery catheter at a location proximal to the proximal end of the proximal cylindrical shaft of the balloon and the distal stent retention band is attached to the inner tube of the stout delivery catheter at a location distal to the distal end of the distal cylindrical shaft of the balloon. A slight gap may be defined between the ends of the mounted stent and the edges of the adjacent stent retention bands. This slight gap may be needed for ease in manufacturing of the stent delivery catheter, for example, as when placing the stent retention bands first and then crimping the stent onto the central cylindrical section of the balloon between the two retention bands. Since the stent length may vary slightly, and the precision for longitudinal placement during crimping is not perfect, the manufacturing process is simplified when the distance between the inner edges of the stent retention bands is slightly longer than the longest stent that will be crimped onto the central cylindrical section of the balloon.

In some examples, the combination of stent retention bands with a stent is placed onto a balloon with only a weak crimping force and/or reduced nesting parameters so as to eliminate damage to any delicate coating on the stent while disallowing stent embolization.

In additional examples, the combination of stein retention bands with a stent is placed onto a balloon with only a weak crimping force and/or reduced nesting parameters for stents that have a polymer with an anti-restenosis drug placed into holes in the stent struts so as to preclude pushing that polymer with drug out of the holes prior to placement of the stout into a vessel of a patient.

In yet further examples, the design improvements as taught herein can be used for at least three types of stent delivery, catheters; namely, 1) over-the-wire stent delivery catheters; 2) rapid exchange stent delivery catheters; and 3) stent-on-a-wire stent delivery catheters as taught in Fischell et al, U.S. Pat. No. 6,375,660, which is hereby incorporated by reference in its entirety.

Another aspect of the disclosure provides a method to prevent the embolization of a stent that has holes containing a polymer that includes an anti-restenosis drug. The method includes a) forming a stent with holes and placing a material containing at least one drug into those holes, b) creating a stent delivery catheter that includes an inflatable balloon that has a proximal stent retention band having a portion that is placed coaxially over the proximal conical section of the balloon and a distal stent retention band having a portion that is placed coaxially over the distal conical section of the balloon, and c) determining what parameters of crimping and nesting can be used which prevent the material with drug from being pushed out of the holes in the struts of the stent, these parameters being a crimping force that does not reduce the final diameter of the portion of the balloon under the stein struts by more than 3.0 mils compared to the diameter of the balloon before the stent is mounted, and nesting parameters that are a pressure less than 10 psi and a temperature that is less than 95 degrees C.

In yet another aspect, a stent delivery catheter includes a catheter tubing defining a lumen therethrough, a balloon disposed near a distal end of the catheter tubing and moving between deflated and inflated states, and proximal and distal stent retention bands concentrically arranged around respective proximal and distal end portions of the balloon. The proximal stent retention band has a distal end located within 2 mm of the proximal end of a stent coaxially received by the balloon and the distal stent retention band has a largest diameter within 2 mm of the distal end of the stent received by the balloon.

In some implementations, each stein retention band comprises an elastic material that expands during inflation of the balloon and contracts upon deflation of the balloon. In some examples, a maximum outer diameter of each stent retention band is within 1.0 mil of an outside diameter of the stent received by the balloon. In additional examples, a maximum outer diameter of each stent retention band is between 1.0 mil and 3.0 mils greater than an outer diameter of the stent received by the balloon. The stent may be received over the balloon with a pressure in the balloon of less than 10 psi and at a temperature of less than 95 degrees C.

Another aspect of the disclosure provides a method of manufacturing a medical device. The method includes disposing a balloon near a distal end of a catheter tubing. The balloon is movable between deflated and inflated states. The method further includes disposing a stent over the balloon and arranging proximal and distal stent retention bands around respective proximal and distal ends of the balloon. The proximal stent retention band has a distal end located within 2 mm of a proximal end of the stent received over the balloon. The distal stent retention band has a largest diameter within 2 mm of a distal end of the stein.

In some implementations, the method includes crimping the stent onto the inflatable balloon such that in a crimped stent state a portion of the balloon under the stent has a outside diameter decreased by less than 2.0 mil with respect to an uncrimped state of the stent. The method may include applying an anti-restenosis compound, such as polylactic acid and/or polyester amide, to the stent. In some examples, the method includes arranging each stent retention band to have an outer diameter within 1.0 mil of an outside diameter of the stent received on the balloon. Moreover, the method may include arranging each stent retention band to have an outer diameter of between 1.0 mil and 3.0 mils greater than an outer diameter of the stent received on the balloon. The stent may be disposed on the balloon while maintaining a pressure in the balloon of less than 10 psi and at a temperature of less than 95 degrees C.

In another aspect, a method of treating vascular stenosis includes inserting into a vessel of a patient a portion of a stent delivery catheter. The stent delivery catheter includes a catheter tubing defining a lumen therethrough, a balloon disposed near a distal end of the catheter tubing and moving between deflated and inflated states, and proximal and distal stent retention bands concentrically arranged around respective proximal and distal end portions of the balloon. The proximal stent retention band has a distal end located within 2 mm of the proximal end of a stent coaxially received by the balloon and the distal stent retention band has a largest diameter within 2 mm of the distal end of the stent received by the balloon. The method further includes advancing the balloon across the vascular stenosis, inflating the balloon to compress the vascular stenosis, deflating the balloon and removing the stent delivery catheter from the patient. A maximum outer diameter of each stent retention band may be within 1.0 mil of an outside diameter of the stent received by the balloon. Moreover, a maximum outer diameter of each stent retention band may be between 1.0 mil and 3.0 mils greater than an outer diameter of the stem received by the balloon.

The details of one or more implementations of the disclosure are set forth in the accompanying drawings and the description below. Other aspects, features, and advantages will be apparent from the description and drawings, and from the claims.

DESCRIPTION OF DRAWINGS

Like reference symbols in the various drawings indicate like elements.

DETAILED DESCRIPTION

Figure 1:
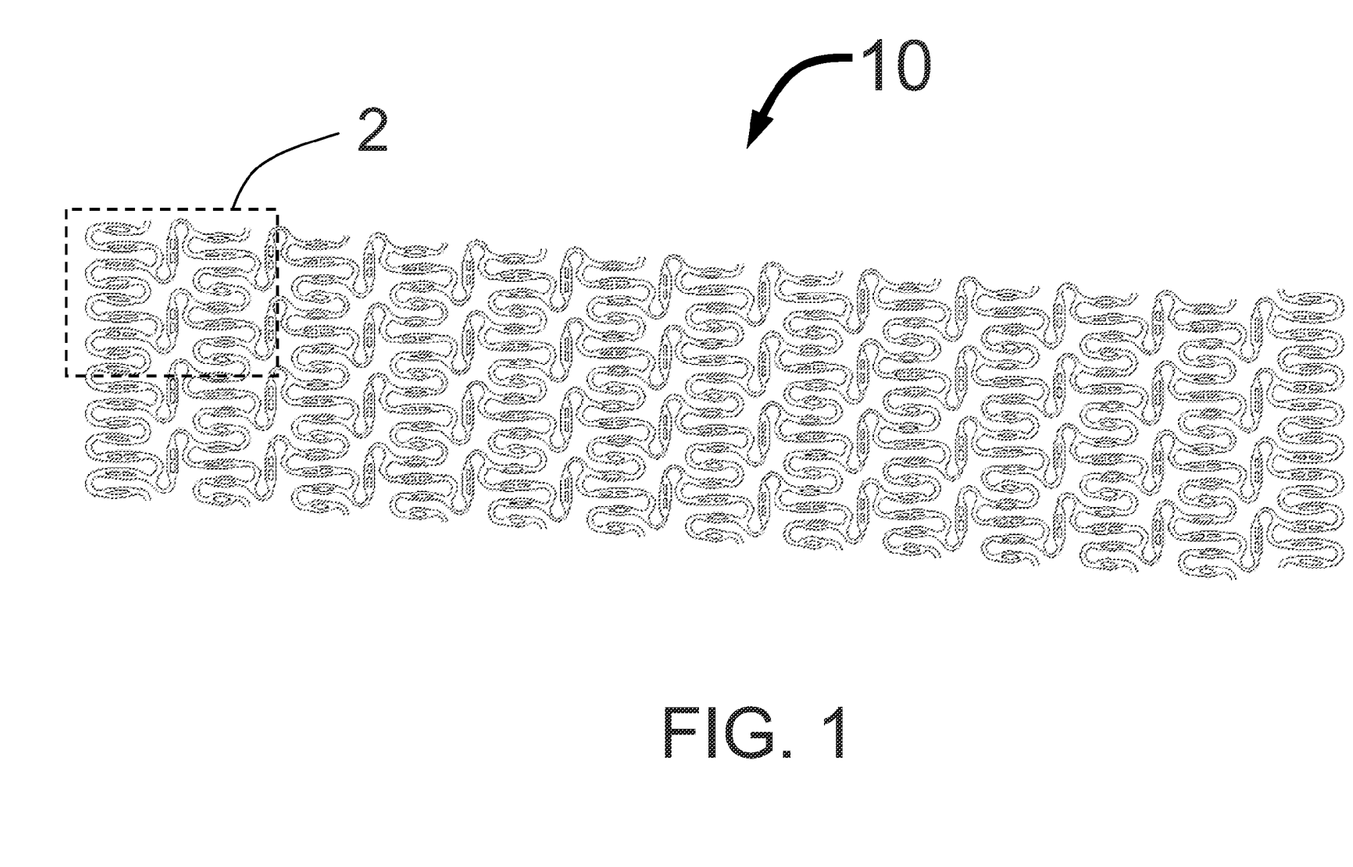
FIG. 1. is a layout drawing of a stent that has holes into which a polymer containing an anti-restenosis drug can be placed.

FIG. 1 provides a flat layout drawing of a stent 10 that defines a multiplicity of elongated holes within wide struts of the stent 10, which holes contain a polymer into which an anti-restenosis drug has been placed.

Figure 2:
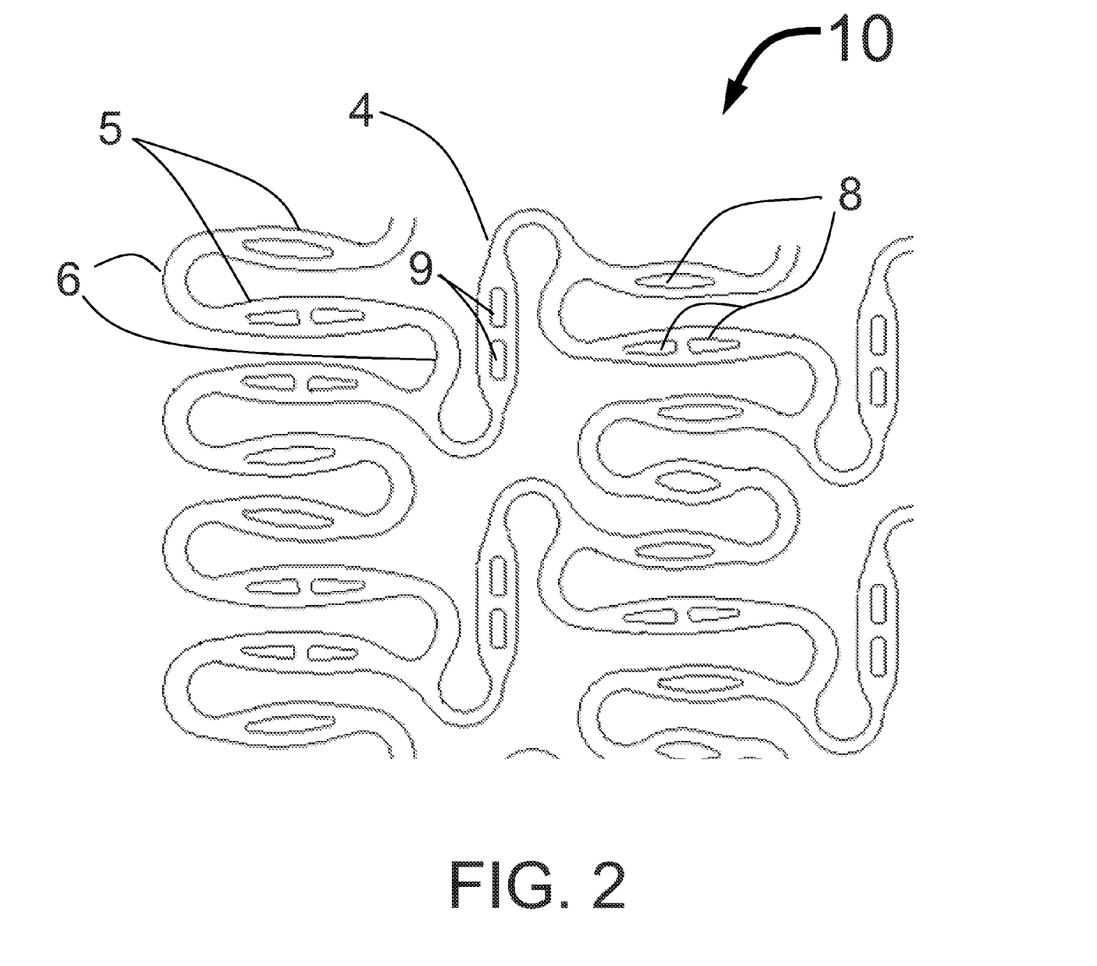
FIG. 2 is an expanded section of the stent, that is shown in FIG. 1.

FIG. 2 provides an enlarged drawing of section 2 of FIG. 1 so as to better understand the details of such a stent design. Specifically, the stent 10, as shown in FIG. 2, shows wide diagonal struts 5 placed between curved crowns 6. The diagonal struts 5 define holes 8 into which a biodegradable material such as polylactic acid (PLGA) or polyester amide (PEA) can be placed. The polymer may include a drug such as sirolimus that is used to prevent restenosis of a stented vessel. Also shown in FIG. 2 are wide undulating connector struts 4 that have holes 9 into which a polymer plus a drug can be placed. Although FIG. 2 shows elongated holes 8, 9 that can have various shapes, these holes could be any similar shapes including circular holes as are currently used for the Nevo® stent manufactured by Cordis Corporation. It is also envisioned that more than one drug or type of drug may be placed into the holes 8, 9 of the stent 10. Multiple drugs may be in a single hole or different drugs in different holes 8, 9.

Figure 3:
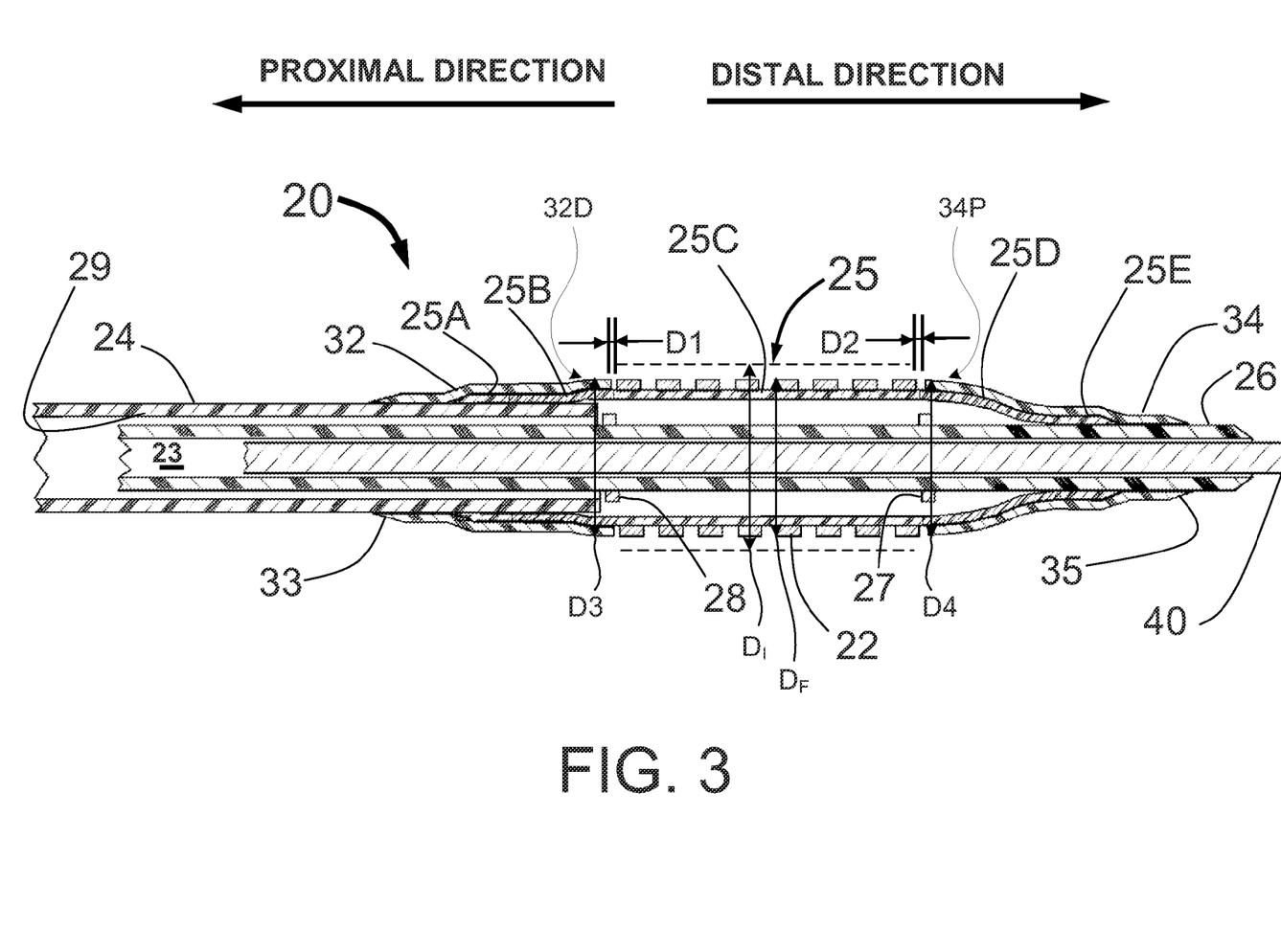
FIG. 3 is a cross-section of a distal portion of a stent delivery catheter.

FIG. 3 is a cross-section of the distal portion of the stent delivery catheter 20. It would be typical of either an over-the-wire stent delivery catheter or a rapid exchange stent delivery catheter to have its distal portion to be formed as is shown in FIG. 3.

The stent delivery catheter 20 illustrated in FIG. 3 has an inner tube 26 that defines an interior lumen 23 through which a guide wire 40 can be placed. Such a stent delivery catheter 20 can be advanced over a guide wire 40 previously placed into a blood vessel of a patient. The stent delivery catheter 20 also has an outer tube 24 which forms a doughnut shaped lumen 29 between the inner surface of the outer tube 24 and the exterior surface of the inner tube 26. This doughnut (toroid) shaped lumen 29 provides a passageway through which pressurized normal saline solution can be used to inflate the balloon 25. The lumen 29 can also used to deflate the balloon 25 after the stent 22 has been placed into a stenosis. In some examples, the stent delivery catheter 20 includes radiopaque marker bands 27, 28 that indicate under fluroscopy the respective proximal and distal ends of the stent 22.

In the example shown, the balloon 25 has five sections which are described (from its proximal end to its distal end) as follows:

1) A proximal cylindrical shaft 25A which defines a cylindrical section fixedly joined to the outer tube 24.

2) A proximal conical section 25B attached at its proximal end to the proximal cylindrical shaft 25A and attached at its distal end to the central cylindrical section 25C of the balloon 25.

3) A central cylindrical section 25C attached at its proximal end to the proximal conical section 25B and attached at its distal end to the distal conical section 25D.

4) A distal conical section 25D attached at its proximal end to the central cylindrical section 25C and attached at its distal end to the distal cylindrical shaft 25E.

5) A distal cylindrical shaft 25E attached at its proximal end to the distal conical section 25D and fixedly joined to a distal portion of the inner tube 26.

Although the proximal conical section 25B is not clearly shown in FIG. 3 to be of a conical shape that it takes when the balloon 25 is inflated. Angioplasty balloons such as the balloon 25 are typically made from a polymeric material such as nylon, formed in their final desired shape and then folded or wrapped to the pre-deployment diameter shown in FIG. 3. In some implementations, the balloon 25 is disposed near a distal end of the inner tube 26 and moves between deflated and inflated states.

Referring again to FIG. 3, in some implementations, the stent delivery catheter 20 includes a proximal stent retention band 32 and a distal stent retention band 34. Although the proximal stent retention band 32 might extend in the proximal direction over only the proximal cylindrical shall 25A of the balloon 25, it may extend over the outer tube 24 creating a smoother transition from the outer tube 24 to the stent 22. Although the distal stent retention band 32 might extend in the distal direction over only the distal cylindrical shaft 25A of the balloon 25, it may extend over the inner tube 24 creating a smoother transition from the inner tube 24 to the stent 22. Smooth transitions in a stent delivery catheter will improve the deliverability of the stent in tortuous vessels of the human body such as the coronary arteries. The stent retention bands 32, 34 can be made from a highly elastic polymer such as polyurethane or silicone rubber.

In some examples, the stent retention bands 32 and 34 are used in conjunction with a stent such as the stent 10 shown in FIGS. 1 and 2. The depicted stent 10 has wide struts that are required if the struts have holes into which a polymer containing a drug is placed. Any stent that has wide struts does not crimp very well onto a balloon so that stent embolization can be a frequent problem. However, the stent retention bands 32, 34, examples of which are shown in FIG. 3, would prevent embolization of any stent whether or not it had wide struts. Moreover, the proximal stent retention band 32 may extend proximal to the balloon proximal shaft 25A and have a tapered proximal end 33 for improving the stent delivery catheter's ability to be easily pulled back into the guiding catheter through which it is placed. The distal stent retention band 34 may extend distally beyond the balloon distal shaft 25E and have a tapered distal end 35 for improving the ability of the stent delivery catheter 20 to be pushed through a tight stenosis. The outside diameter of the distal stent retention band 34 may be equal to or greater than the diameter of the stent 22, thus creating a continuous outer surface of the stent delivery catheter 20 and improving the ability of the stein delivery catheter 20 to penetrate through a tight stenosis or navigate around a sharp bend.

The proximal and distal stent retention bands 32, 34 can be concentrically arranged around a respective proximal end portion (e.g., the proximal cylindrical shaft 25A and/or the proximal conical section 2513) and a respective distal end portion (e.g., the distal conical section 25D and/or the distal cylindrical shaft 25E) of the balloon 25. The proximal stent retention band 32 can have a distal end 32D located within 2 mm of the proximal end of a stent 10, 22 coaxially received by the balloon 25 and the distal stent retention band 34 can have a largest diameter within 2 mm (e.g., at a proximal end 34P of the distal stent retention band 34) of the distal end of the stent 10, 22. Each stent retention band 32, 34 may comprise an elastic material that expands during inflation of the balloon 25 and contracts upon deflation of the balloon 25. In some examples, a maximum outer diameter D3, D4 of each stent retention band 32, 34 is within 1.0 mil of an outside diameter $D_F$ of the stein 22 (e.g., the diameter of the stent in a crimped state) received by the balloon 25. In additional examples, a maximum outer diameter D3, D4 of each stent retention band 32, 34 is between 1.0 mil and 3.0 mils greater than an outer diameter $D_F$ of the stent 22 received by the balloon 25. The stent 22 may be received over the balloon 25 with a pressure in the balloon 25 or less than 10 psi and at a temperature of less than 95 degrees C.

The stout retention bands 32, 34, as arranged on the stent delivery catheter 20, can be used to prevent stent embolization for any stent that has holes, such as the stents shown in FIGS. 1 and 2 or the round holes used by the Nevo stent. This is because only a weak crimping force and/or reduced nesting parameters can be utilized to mount such a stent without pushing the polymer with drug out of the holes.

The stein retention bands 32, 34 may have one or more of the following advantages: (1) refolding the balloon after it is inflated; (2) preventing bulging at the ends of the balloon during stent expansion (which is called "dog-boning,") which can cause arterial restenosis; (3) providing a smooth tapered leading edge stent delivery system 20 so that the stent more easily can be pushed through a tight stenosis or around tight bends; (4) making it is easier to push the stent 22 through a tight stenosis, for example, by having an outside diameter of the distal stent retention band 34 that is greater than the outside diameter of the stent 22 so that there is not a step up in diameter for the stent 22 as is the case for conventional balloon expandable stent delivery systems; and (5) keeping the stent 22 positioned onto only the central cylindrical section 25C of the balloon 25 using the interior edges of both retention bands 32, 34 so that the stent 22 stays over the central cylindrical section 25C of the balloon and is properly deployed when the balloon 25 is inflated. Thus, the stent retention bands 32, 34 can provide a multiplicity of advantages for the stent delivery catheter 20.

Depending on the sizes and shapes of the holes in the struts of stents such as those shown in FIGS. 1 and 2, a stent manufacturer would have to determine experimentally what parameters could be used to seat the stent onto the balloon without causing the polymer in the holes to be pushed out. Usage of the stent retention bands 32, 34 can significantly reduce these parameters compared to what is used for bare metal stents. Thus, a method to prevent the polymer-plus-drug from popping out of holes in the stent's struts can determine the crimping and/or nesting parameters that provides adequate attachment of the stent to the balloon without causing any polymer to pop out of its hole. In some implementations, a method to prevent the embolization of a stent that has holes containing a polymer that includes an anti-restenosis drug includes a) forming a stent 22 with holes and placing a material containing at least one drug into those holes, b) creating a stent delivery catheter 20 that includes an inflatable balloon 25 that has a proximal stent retention band 32 having a portion that is placed coaxially over the proximal conical section 25B of the balloon 25 and a distal stent retention band 34 having a portion that is placed coaxially over the distal conical section 25D of the balloon 25, c) determining (e.g., by experimentation) what parameters of crimping and nesting can be used which prevent the material with drug from being pushed out of the holes 8, 9 in the struts 5 of the stent 10, 20, these parameters being a crimping force that does not reduce the final diameter $D_F$ of the portion of the balloon 25 under the stent struts 5 by more than 3.0 mils compared to the diameter $D_I$ of the balloon before the stent 10, 20 is mounted, and nesting parameters that are a pressure less than 10 psi and a temperature that is less than 95 degrees C.

In some examples, a weak crimping force is a force that only decreases the final diameter $D_F$ (after crimping and nesting are completed) of the portion of the balloon 25 that is under a stent strut by approximately 1.0 mil to 2 mils compared to the outside diameter $D_I$ of the balloon 25 before the stent 22 is mounted. This final diameter $D_F$ is much less (e.g., 20%-50%) for the balloon diameter decrease (e.g., 3.0 mils or more) that is used with typical crimping processes. In some implementations, the reduced nesting parameters includes having either a reduced pressure that is less than 10 psi, and/or a reduced temperature that is less than 95 degrees C., and/or a reduced nesting time that is less than 20 seconds, or any combination of these nesting parameters that would disallow the popping out of the polymer plus drug from holes 8, 9 in a stent strut 5. The method for determining acceptable parameters for crimping and nesting can be experimentally accomplished. The value of these parameters may depend upon the size and shape of the hole, the thickness of the stent's struts, the type of polymer and drug that is used.

As can be seen in the example shown in FIG. 3, a small distance D1 may separate the distal end of the proximal stein retention band 32 from the proximal end of the stent 22 and a distance D2 that separates the proximal end of the distal stent retention band 34 from the distal end of the stent 22. This differs from the system shown in the Fischell patents (noted earlier), where the stent ends touch the edges of the stent retention bands. In some implementations, each of the separation distances D1 and D2 are greater than 0.1 mm and less than 2.0 mm. The purpose of these separation distances D1 and D2 can be to allow for uncertainly in manufacturing for the actual length of the stents 22 compared with the actual separation distance D1 and D2 between the inner edges of the stent's stent retention bands 32, 34. In addition, the distances D1 and D2 reduce the need for longitudinal positional accuracy as the stent 22 is crimped down onto the balloon 25 in manufacturing the product.

In some implementations, the proximal stent retention band 32 is adhesively attached to the stent delivery system 20 proximal to the balloon proximal conical section 25B. For example, the proximal stent retention band 32 can be fixedly attached to both the outer tube 24 and the balloon proximal cylindrical shaft 25A, but not attached to the balloon's proximal conical section 25B. During balloon inflation, the balloon 25, including the proximal conical section 25B, can unfold and slide underneath the portion of the proximal stent retention band 32 that lies over the proximal conical section 25B of the balloon 25.

Similarly, in some implementations, the distal stent retention band 34 is adhesively attached to the stent delivery system 20 distal to the balloon distal conical section 25D. For example, the distal stent retention band 34 can be fixedly attached to both the inner tube 26 and the balloon distal cylindrical shaft 25E, but not attached to the balloon distal conical section 25D. During balloon inflation, the balloon 25 including the distal conical section 25D can unfold and slide underneath the portion of the distal stent retention band 34 that lies over the distal conical section 25D of the balloon 25.

In some implementations, the method includes crimping the stent onto the inflatable balloon such that in a crimped stent state a portion of the balloon under the stent has a outside diameter decreased by less than 2.0 mil with respect to an uncrimped state of the stent. The method may include applying an anti-restenosis compound, such as polylactic acid and/or polyester amide, to the stent. In some examples, the method includes arranging each stent retention band to have an outer diameter within 1.0 mil of an outside diameter of the stent received on the balloon. Moreover, the method may include arranging each stent retention band to have an outer diameter of between 1.0 mil and 3.0 mils greater than an outer diameter of the stent received on the balloon. The stent may be disposed on the balloon while maintaining a pressure in the balloon of less than 10 psi and at a temperature of less than 95 degrees C.

In another aspect, a method of treating vascular stenosis includes inserting into a vessel of a patient a portion of a stent delivery catheter. The stent delivery catheter includes a catheter tubing defining a lumen therethrough, a balloon disposed near a distal end of the catheter tubing and moving between deflated and inflated states, and proximal and distal stent retention bands concentrically arranged around respective proximal and distal end portions of the balloon. The proximal stent retention band has a distal end located within 2 mm of the proximal end of a stent coaxially received by the balloon and the distal stent retention band has a largest diameter within 2 mm of the distal end of the stent received by the balloon. The method further includes advancing the balloon across the vascular stenosis, inflating the balloon to compress the vascular stenosis, deflating the balloon and removing the stent delivery catheter from the patient. A maximum outer diameter of each stent retention bands may be within 1.0 mil of an outside diameter of the stent received by the balloon. Moreover, a maximum outer diameter of each stent retention bands may be between 1.0 mil and 3.0 mils greater than an outer diameter of the stent received by the balloon.

Another aspect of the disclosure provides a method of manufacturing a medical device. The method includes disposing a balloon near a distal end of a catheter tubing. The balloon is movable between deflated and inflated states. The method further includes disposing a stent over the balloon and arranging proximal and distal stent retention bands around respective proximal and distal ends of the balloon. The proximal stent retention band has a distal end located within 2 mm of a proximal end of the stent received over the balloon. The distal stent retention band has a largest diameter within 2 mm of a distal end of the stent.

In some implementations, the method includes crimping the stent onto the inflatable balloon such that in a crimped stent state a portion of the balloon under the stent has a outside diameter decreased by less than 2.0 mil with respect to an uncrimped state of the stent. The method may include applying an anti-restenosis compound, such as polylactic acid and/or polyester amide, to the stent. In some examples, the method includes arranging each stent retention band to have an outer diameter within 1.0 mil of is an outside diameter of the stent received on the balloon. Moreover, the method may include arranging each stent retention band to have an outer diameter of between 1.0 mil and 3.0 mils greater than an outer diameter of the stent received on the balloon. The stent may be disposed on the balloon while maintaining a pressure in the balloon of less than 10 psi and at a temperature of less than 95 degrees C.

In another aspect, a method of treating vascular stenosis includes inserting into a vessel of a patient a portion of a stent delivery catheter. The stent delivery catheter includes a catheter tubing defining a lumen therethrough, a balloon disposed near a distal end of the catheter tubing and moving between deflated and inflated states, and proximal and distal stent retention bands concentrically arranged around respective proximal and distal end portions of the balloon. The proximal stent retention band has a distal end located within 2 mm of the proximal end of a stent coaxially received by the balloon and the distal stent retention band has a largest diameter within 2 min of the distal end of the stent received by the balloon. The method further includes advancing the balloon across the vascular stenosis, inflating the balloon to compress the vascular stenosis, deflating the balloon and removing the stent delivery catheter from the patient. A maximum outer diameter of each stent retention bands may be within 1.0 mil of an outside diameter of the stent received by the balloon. Moreover, a maximum outer diameter of each stent retention bands may be between 1.0 mil and 3.0 mils greater than an outer diameter of the stent received by the balloon.

In some implementations, a method of manufacturing a medical device includes disposing a balloon 25 near a distal end of a catheter tubing, such as the inner tube 26. The balloon 25 is movable between deflated and inflated states. The method further includes disposing a stent 22 over the balloon 25 and arranging proximal and distal stent retention bands 32, 34 around respective proximal and distal ends of the balloon 25. The proximal stent retention band 32 has a distal end 32D located within 2 mm of a proximal end of the stent 22 received over the balloon 25. The distal stent retention band 34 has a largest diameter D4 within 2 mm of a distal end of the stent 22.

In some implementations, the method includes crimping the stent 22 onto the inflatable balloon 25 such that in a crimped stent state a portion of the balloon 25 under the stent 22 has a outside diameter $D_F$ decreased by less than 2.0 mil with respect to an initial diameter $D_I$ of the stent 22 in an uncrimped state of the stent. The method may include applying an anti-restenosis compound, such as polylactic acid and/or polyester amide, to the stent. In some examples, the method includes arranging each stent retention band 32, 34 to have its respective outer diameter D3, D4 within 1.0 mil of an outside diameter $D_F$ of the stent 22 received on the balloon 25. Moreover, the method may include arranging each stent retention band 32, 34 to have an outer diameter D3, D4 of between 1.0 mil and 3.0 mils greater than an outer diameter of the stent 22 received on the balloon 25. The stent 22 may be disposed on the balloon 25 white maintaining a pressure in the balloon 25 of less than 10 psi and at a temperature of less than 95 degrees C.

A method of treating vascular stenosis, in some examples, includes inserting into a vessel of a patient a portion of a stent delivery catheter 20. The stent delivery catheter 20 includes a catheter tubing defining a lumen therethrough, a balloon 25 disposed near a distal end of the catheter tubing and moving between deflated and inflated states, and proximal and distal stent retention bands 32, 34 concentrically arranged around respective proximal and distal end portions of the balloon 25. The proximal stent retention band 32 has a distal end 32D located within 2 mm of the proximal end of a stent 22 coaxially received by the balloon 25 and the distal stent retention band 34 has a largest diameter within 2 mm of the distal end of the stent 22 received by the balloon 25. The method further includes advancing the balloon 25 across the vascular stenosis, inflating the balloon 25 to compress the vascular stenosis, deflating the balloon 25 and removing the stent delivery catheter 20 from the patient. A maximum outer diameter of each stent retention band 32, 34 may be within 1.0 mil of an outside diameter $D_F$ of the stent 22 received by the balloon 25. Moreover, a maximum outer diameter D3, D4 of each stent retention band 32, 34 may be between 1.0 mil and 3.0 mils greater than an outer diameter $D_F$ of the stent 22 received by the balloon 25.

A number of implementations have been described. Nevertheless, it will be understood that various modifications may be made without departing from the spirit and scope of the disclosure. Accordingly, other implementations are within the scope of the following claims.

What is claimed is:

1. A stent delivery catheter comprising:
   an inflatable balloon having a central cylindrical section, a distal portion having a distal conical section and a distal cylindrical shaft and a proximal portion having a proximal conical section and a proximal cylindrical shaft;
   a drug eluting stent coaxially mounted over the central cylindrical section of the inflatable balloon, the drug eluting stent having a proximal end and a distal end;
   an inner tube having a central guide wire lumen designed to be advanced over a guide wire, the inner tube being attached near its distal end to the distal cylindrical shaft of the inflatable balloon;
   an outer tube that is fixedly attached at or near its distal end to the proximal cylindrical shaft of the inflatable balloon;
   a distal stent retention band having a generally conical shape and mounted onto the distal portion of the inflatable balloon, the distal stent retention band having its smallest diameter just proximal to the distal end of the inner tube and having its largest diameter at its proximal end, the proximal end of the distal stent retention band separated in a distal direction from the distal end of the drug eluting stent by a separation distance between 0.1 and 2 mm when the inflatable balloon is in an uninflated state; and
   a proximal stent retention band mounted coaxially over the proximal portion of the balloon, the proximal stent retention band having its distal end separated in a proximal direction from the proximal end of the drug eluting stent by a separation distance between 0.1 mm and 2 mm when the inflatable balloon is in the uninflated state;
   wherein the drug eluting stent is coaxially mounted over the central cylindrical section of the inflatable balloon between the proximal end of the distal stent retention band and the distal end of the proximal stent retention band, the drug eluting stent being crimped onto the inflatable balloon with a moderate crimping force that is such that after manufacturing is completed, a final outside diameter of the portion of the balloon that is under the stent struts is less than a 2.0 mil decrease from the balloon outside diameter just before the drug eluting stent is mounted.

2. The stent delivery catheter of claim 1, where a maximum outer diameter of the stent retention bands is within 1.0 mil of an outside diameter of the drug eluting stent mounted onto the inflatable balloon.

3. The stent delivery catheter of claim 1, where a maximum outer diameter of the stent retention bands is between 1.0 mil and 3.0 mils greater than an outer diameter of the drug eluting stent as it is mounted onto the inflatable balloon.

4. The stent delivery system of claim 1, further including the stent being nested with a pressure in the balloon that is less than 10 psi and a temperature that is less than 95 degrees C.

5. A stent delivery catheter comprising:
   a catheter tubing defining a lumen therethrough, the tubing having a proximal end and a distal end;
   a balloon disposed near a distal end of the catheter tubing and moving between deflated and inflated states;
   proximal and distal stent retention bands concentrically arranged around respective proximal and distal end portions of the balloon, the proximal and distal stent retention bands each having a proximal end and a distal end, the distal stent retention band comprises a smallest diameter just proximal the distal end of the catheter tubing and comprises a largest diameter at its proximal end; and
   a drug eluting stent coaxially received by the balloon and mounted over the balloon between the proximal and distal stent retention bands, the drug eluting stent having a proximal end and a distal end;
   wherein the distal end of the proximal stent retention band is separated in a proximal direction from the proximal end of the drug eluting stent by a separation distance between 0.1 mm and 2 mm and the proximal end of the distal stent retention band separated in a distal direction from the distal end of the drug eluting stent by a separation distance between 0.1 mm and 2 mm when the balloon is deflated.

6. The stent delivery catheter of claim 5, wherein each stent retention band comprises an elastic material that expands during inflation of the balloon and contracts upon deflation of the balloon.

7. The stent delivery catheter of claim 5, wherein a maximum outer diameter of each stent retention band is within 1.0 mil of an outside diameter of the stent received by the balloon.

8. The stent delivery catheter of claim 5, wherein a maximum outer diameter of each stent retention band is between 1.0 mil and 3.0 mils greater than an outer diameter of the stent received by the balloon.

9. The stent delivery system of claim 5, wherein the stent is received over the balloon with a pressure in the balloon of less than 10 psi and at a temperature of less than 95 degrees C.

\* \* \* \* \*